United States Patent [19]
Babler

[11] Patent Number: 5,471,005
[45] Date of Patent: Nov. 28, 1995

[54] METHOD OF MAKING 2,7-DIMETHYL-2,4,6-OCTATRIENEDIAL, A KEY INTERMEDIATE IN THE COMMERCIAL SYNTHESES OF VARIOUS CAROTENOIDS

[75] Inventor: James H. Babler, Chicago, Ill.

[73] Assignee: Loyola University of Chicago, Chicago, Ill.

[21] Appl. No.: 339,659

[22] Filed: Nov. 18, 1994

[51] Int. Cl.$^6$ ............................ C07C 47/20; C07C 45/61
[52] U.S. Cl. .................... 568/459; 568/448; 568/458; 568/466
[58] Field of Search .................... 568/448, 458, 568/459, 466

[56] References Cited

U.S. PATENT DOCUMENTS

| | | | |
|---|---|---|---|
| 4,010,207 | 3/1977 | Hall et al. | 568/458 |
| 4,196,151 | 4/1980 | Suyama et al. | 568/459 |
| 5,107,030 | 4/1992 | Babler | 568/494 |

FOREIGN PATENT DOCUMENTS

| | | |
|---|---|---|
| 866691 | 4/1961 | United Kingdom . |

OTHER PUBLICATIONS von Zeller et al., "Synthesen in de Carotinoid–Reihe," *Helvetica Chimica Acta*, vol. XLII, No. 91–92, pp. 841–853, 1959.

Aliphatic Compounds, *Chem. Abstracts*, 54, (1960).

Powers et al., "The Reaction of Formates and Formamides with Base," Contribution No. 1965 from the Department of Chemistry, UCLA, pp. 2623–2627, 1966.

Newman et al., "High–Dilution Cyclization of Polyoxapentacosanodinitriles," *J. Org. Chem.*, 40:20, pp. 2863–2870, 1975.

Villagòmex–Ibarra et al., "Synthèse Totale de la (±)–Parvifoline," *Tetradedron Letters*, 35:27, pp. 4771–4772, 1994.

*Chemical Abstracts*, 58, 4428d (1961).

*Primary Examiner*—Werren B. Lone
*Attorney, Agent, or Firm*—Marshall, O'Toole, Gerstein, Murray & Borun

[57] ABSTRACT

A procedure for forming methylmalonaldehyde from propionaldehyde, an alkyl formate and a sodium alkoxide, utilizing a crossed-Claisen condensation is disclosed. The procedure avoids the formation of aldol condensation products. Also disclosed are processes for preparing 3-alkoxy-2-methylpropenals such as 2-methyl-3-(2-methyl-2-propenoxy)propenal from methylmalonaldehyde. The latter products are useful in the synthesis of carotenoids.

21 Claims, No Drawings

METHOD OF MAKING 2,7-DIMETHYL-2,4,6-OCTATRIENEDIAL, A KEY INTERMEDIATE IN THE COMMERCIAL SYNTHESES OF VARIOUS CAROTENOIDS

BACKGROUND OF THE INVENTION

The present invention describes processes for preparing 3-alkoxy-2-methylpropenals of the formula $$ROCH=\underset{\underset{CH_3}{|}}{C}-CH=O$$

wherein R is selected from the group consisting of $C_1$–$C_{10}$ alkyl, benzyl, 2-propenyl (allyl), and 2-methyl-2-propenyl (methallyl). Preferred "R groups" include: methyl, ethyl, propyl, isopropyl, butyl, isobutyl, sec-butyl, allyl, and methallyl. These propenals are also referred to as 3-alkoxymethacroleins and monoenol ether derivatives of methylmalonaldehyde.

Isler, et al have described a procedure wherein 3-ethoxymethacrolein (5), a representative 3-alkoxy-2-methylpropenal, was converted in high yield to 2,7-dimethyl-2,4,6-octatrienedial (a C-10 dialdehyde); see, British patent 866,691 (Apr. 26, 1961). This C-10 dialdehyde is an essential intermediate in the industrial synthesis of many carotenoids, which have found increasing uses in the coloration of foodstuffs and pharmaceuticals and in animal feedstocks. Beta-carotene, a yellow food dye added to oleomargarine among other items, is a representative of this group of naturally occurring compounds, and is illustrated by Formula 1:

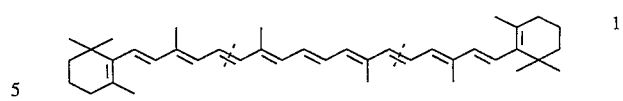

Other commercially-important carotenoids are canthaxanthin (used commercially as a feed additive and also as a red color additive for food and drugs) and astaxanthin (the red skin pigment of salmon, lobster and trout, and now of increasing importance in the fish-farming industry).

Published syntheses of beta-carotene and related carotenoids have advantageously used the symmetry of the compound to develop convergent synthetic schemes to make the compound. In particular, the ten carbon atom fragment in the center of the compound (the fragment included within the dashed lines as illustrated in Formula 1) has been used in known synthetic schemes. Various methods for preparing this ten carbon atom fragment are described by Isler, *Carotenoids*, Birkhauser-Verlag, 431–436 (1971).

As noted above, a known preparation of the ten carbon fragment, 2,7-dimethyl-2,4,6-octatrienedial, was developed by O. Isler and his co-workers at Hoffmann-LaRoche. The Roche process, described in O. Isler, et al, *Helv. Chim. Acta*, 42, 841–853 (1959) and British Patent 866,691, is schematically outlined in Scheme I, and uses 3-ethoxmethacrolein (5) as a key intermediate. This expensive specialty chemical (5) is now available from Aldrich Chemical Co., et al.

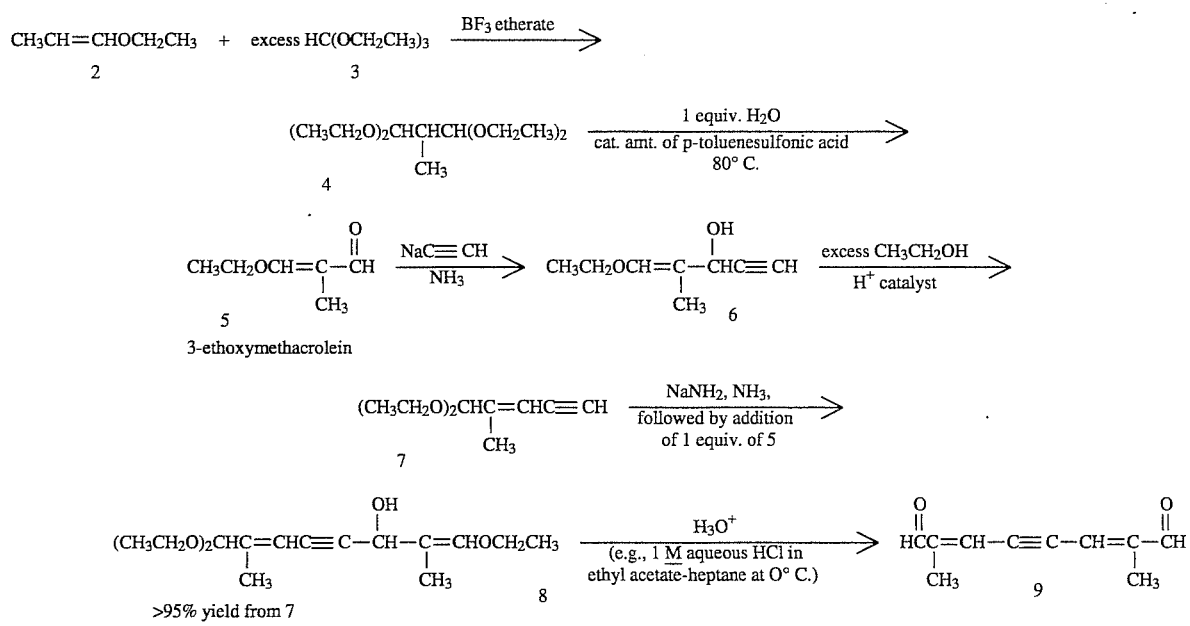

The bis(diethyl acetal) derivative of dialdehyde 9 has been prepared from intermediate 8 as shown below:

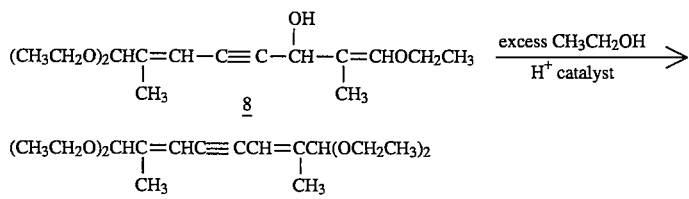

This latter bisacetal can be subsequently hydrolyzed using weakly acidic conditions (e.g., acetic acid and water) to obtain dialdehyde 9. See Example XXVI in U.S. Pat. No. 5,107,030 (Apr. 21, 1992) for a similar procedure.

Dialdehyde 9 can be partially hydrogenated as follows:

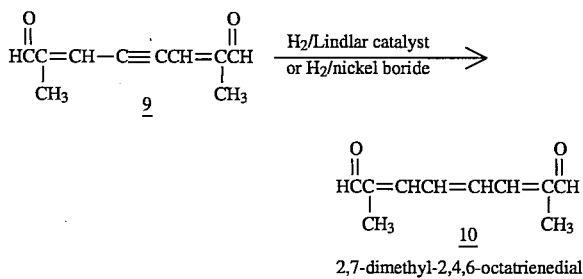

2,7-dimethyl-2,4,6-octatrienedial

Alternatively, partial hydrogenation of the triple bond in alkyne 9 can be delayed until after the total synthesis of the C-40 carotenoid structure.

The principal disadvantage of the above procedure for forming dialdehyde 10 arises from the cost and method of preparation of the raw materials (2 and 3) required in the first step: 1-ethoxypropene (2) is an expensive, acid-sensitive specialty chemical; and triethyl orthoformate (3) (required in excess) is both costly and requires the toxic chemical chloroform for its manufacture.

BRIEF DESCRIPTION OF THE INVENTION

The present invention is directed to methods of forming vinylogous esters such as (5) (i.e., 3-alkoxy-2-methylpropenals). The procedure employs inexpensive reactants with relatively low toxicity—methyl formate, propionaldehyde and various low molecular weight alcohols (e.g., ethyl alcohol and 1-butanol). Another advantage is the fact that all waste by-products are "environmentally-friendly": alcohol and sodium chloride (or sodium bromide).

The synthesis route of the present invention is outlined in Scheme II, wherein step (a) is a condensation reaction, and step (b) is an alkylation reaction involving the conversion of the product of step (a) to a 3-alkoxy-2-methylpropenal.

Scheme II

Step (a)

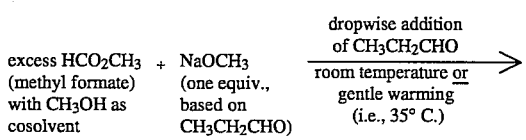

-continued
Scheme II

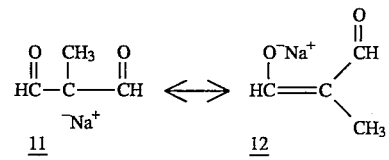

The sodium salt (i.e., enolate anion 11 and 12) of methylmalonaldehyde has been previously prepared using 1-ethoxypropene and triethyl orthoformate (see: *Chem. Abstracts*, 54, 20870a (1960)).

Structures 11 and 12 are the two contributors to the resonance hybrid representing the anion of methylmalonaldehyde (i.e., the anion of 2-methylpropanedial). Although methyl formate is the preferred reactant/solvent for this process, this step can also be effected using other ester derivatives of formic acid such as ethyl formate, propyl formate and butyl formate, and the generic reaction written:

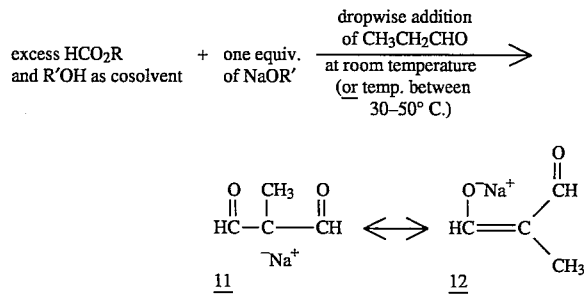

The above reaction proceeds at temperatures in the range of from about 15° C. to about 50° C.

The amount of propionaldehyde employed in the reaction should not exceed the molar amount of the sodium alkoxide in the reaction mixture (i.e., one equivalent or less). Moreover, in order to avoid aldol condensation, the amount of propionaldehyde in the reaction mixture should be kept very low—using dropwise addition of the propionaldehyde, or some other procedure which will maintain the molar ratio of formate ester to propionaldehyde in the reaction mixture at a level greater than 5000:1. Besides dropwise addition, use of a reaction apparatus similar to the one described on page 2864 of an article by M. S. Newman, et al, *J. Org. Chem.*, 40, 2863–2870 (1975) should enable one to add a solution of propionaldehyde in alkyl formate to the base/alkyl formate reaction mixture under "high-dilution conditions" without the need for large volumes of solvent.

NaOR' can be prepared, in situ, by the addition of metallic sodium to R'OH. The excess $C_1$–$C_4$ formate used in this process is recyclable since it can be removed by simple distillation once the addition of propionaldehyde has been completed. Alcohol (R'OH) is necessary as a cosolvent, since, in its absence, the sodium alkoxide base: catalyzes the slow decomposition of formate esters (see: J. C. Powers, et al, *J. Org. Chem.*, 31, 2623 (1966) and references therein).

The process of Step (a) of Scheme II, which involves the reaction of a formate ester and a carbonyl compound, is known as a crossed-Claisen condensation. This process is well known for ketones, but is disfavored for enolizable aldehydes since self-aldol condensation of the latter is a very facile process. Examples of crossed-Claisen condensations of ketones such as acetone and cyclohexanone with ethyl formate are found in *Organic Syntheses,* Collective Volume IV, pp. 210 and 536. Use of a similar procedure with propionaldehyde led to self-aldol condensation of the latter. (See Example III, infra).

Step (b) of Scheme II is as follows:

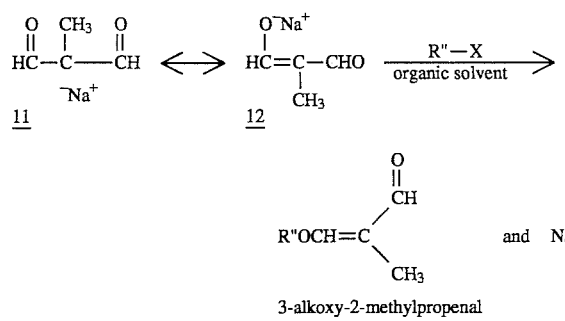

As described in greater detail below, despite the presence of two reactive species (11 and 12), the products of the foregoing reaction are exclusively the "O-alkylation" product, a 3-alkoxy-2-methylpropenal, rather than the "C-alkylation" product of species 11.

In the foregoing alkylation reaction, R"—X represents a $C_1$–$C_{10}$ alkyl, benzyl or unsaturated halide: X=bromine or chlorine and R"=$C_1$–$C_{10}$ alkyl, $C_3$–$C_{10}$ allylic or benzyl. Preferred "R" groups" include methyl, ethyl, propyl, isopropyl, butyl, isobutyl, sec-butyl, 2-propenyl (allyl) and 2-methyl-2-propenyl (methallyl). Preferred R"—X compounds include: 1-bromobutane, 1-chlorobutane, 1-bromopropane, 1-chloropropane, 1-bromoethane, allyl chloride and methallyl chloride (3-chloro-2-methylpropene).

In lieu of R"—X for this alkylation step, one can use sulfate esters derived from simple alcohols:

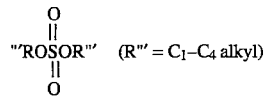

Preferred sulfate esters include dimethyl sulfate and diethyl sulfate.

The alkylation step can be conducted in the same reaction vessel used to prepare the sodium salt of methylmalonaldehyde (11 and 12)—i.e., the latter need not be isolated. Indeed, due to the instability of methylmalonaldehyde, it is generally desirable not to attempt to isolate the product from the step (a) reaction mixture.

The organic solvent utilized in this alkylation step is preferably a polar, aprotic solvent such as N,N-dimethylformamide, acetonitrile, 1,4-dioxane and 1-methyl-2-pyrrolidinone. Although an aprotic solvent is preferred, the solvent does not need to be aprotic, since the presence of alcohol (present when 11 and 12 were formed in the crossed-Claisen condensation) in the reaction mixture did not prevent the successful execution of this alkylation step—although, in its presence, alkylation occurred more slowly. Furthermore, mixtures of solvents can be utilized with no substantial loss of the desired 3-alkoxy-2-methylpropenal—e.g., nonpolar solvents such as benzene, toluene or xylene can be used as cosolvents with a polar organic solvent such as N,N-dimethylformamide.

A preferred procedure is to remove the residual alkyl formate and alcohol at the conclusion of the step (a) reaction prior to proceeding with alkylation step (b). For example, if methyl formate and methanol are employed in the step (a) procedure, a nonpolar organic solvent (e.g., benzene) can be added to the step a reaction vessel and the mixture heated to a temperature in excess of 35° C. to remove the remaining methyl formate by distillation. Next, a polar, aprotic solvent (e.g., N,N-dimethylformamide) can be added to the reaction vessel and the step (a) reaction product heated to a temperature above 65° C. to remove residual methyl alcohol. Although these distillation steps are not required, they will increase the rate of the step (b) (alkylation) reaction.

The reaction temperature for the alkylation step varies with the reagent utilized: reaction with dimethyl sulfate can occur at room temperature; reactions with allylic chlorides were generally conducted at 40°–50° C.; the less reactive 1° alkyl bromides (e.g., 1-bromopropane) were utilized in this process at higher temperatures: 60°–70° C., and the sluggish 2° alkyl chlorides required heating the mixture to temperatures of 60°–100° C. to accelerate the alkylation.

Alkylations of this type have been reported; however, the exclusive formation of the O-alkylation product (derived from 12) using a variety of alkyl halides and various solvent mixtures was unexpected. The C-alkylation product

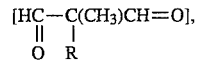

derived from species 11, is generally observed along with the O-alkylation product when anions derived from beta-dicarbonyl compounds are alkylated. See examples cited in: F. A. Carey and R. J. Sundberg, *Advanced Organic Chemistry, Part B: Reactions and Synthesis,* Third edition (Plenum Press, 1990), pp. 23–25. Even the hindered 3° carbanion derived from 2-methyl-1,3-cyclopentanedione undergoes C-alkylation (see: P. Joseph-Nathan, et al, *Tetrahedron Lett.,* 35, 4771 (1994)). As noted above, the process described herein produces the desired O-alkylation product exclusively.

If one desires to avoid the use of alkyl halides in the overall process used to obtain 3-alkoxy-2-methylpropenals, the sodium salt of methylmalonaldehyde (11 and 12) can alternatively be acidified and subsequently treated with a $C_1$–$C_4$ primary or secondary alcohol (e.g., isobutyl alcohol) at elevated temperatures (75°–100° C.) with simultaneous removal of water from the reaction mixture:

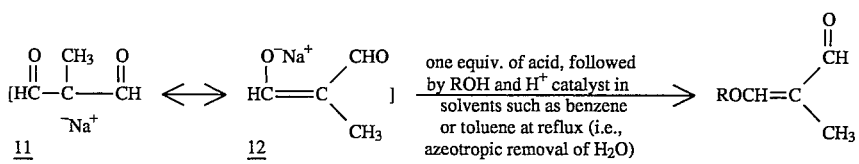

Suitable acids have a $pk_a<5$, e.g., acetic acid, formic acid, p-toluenesulfonic acid, benzoic acid, maleic acid, and inorganic acids such as hydrochloric acid, sulfuric acid, nitric acid, etc. (These strong mineral acids may have a $pk_a$ of less than zero). An example of this type of transformation is shown at Example VII.

Observations on Process (a) The yield of the desired 3-alkoxy-2-methylpropenal was low (<25%) and several unidentified by-products were obtained when $KOCH_3$ (potassium methoxide) was used as the base in lieu of $NaOCH_3$.

(b) The lack of C-alkylation products when the sodium salt of methylmalonaldehyde was alkylated under a variety of conditions was unexpected (see the references listed in Carey & Sundberg's textbook, cited above).

(c) That conditions could be found to effect a crossed-Claisen condensation between an enolizable aldehyde such as propionaldehyde and methyl formate was unexpected. Even in experiments utilizing 100 equivalents of methyl formate (vs. propionaldehyde), the major reaction observed was the self-aldol condensation of propionaldehyde.

The conditions required to minimize (or avoid) a facile aldol condensation of propionaldehyde involved dropwise addition of propionaldehyde to an amount of formate ester given by the following: x+>5,000 y; where x=moles of propionaldehyde and y=amount (i.e., in micromoles or millimoles) of propionaldehyde in each small portion (i.e., each drop) of propionaldehyde added. The rate of addition of propionaldehyde to the methyl formate/base mixture should be such that propionaldehyde is present only in low concentration—i.e., always less than 0.01M with respect to the volume of methyl formate present in the mixture at the time of addition. However, the time interval between these additions of small amounts of propionaldehyde can be quite small, since the crossed-Claisen condensation occurs nearly instantaneously at room temperature.

As a consequence, this process is actually easier to conduct on a large scale than on a micro scale; and since the product of the crossed-Claisen condensation is instantaneously converted to an anion (structures 11 and 12), the first step is essentially irreversible. At the instant that small amounts of propionaldehyde are added to the reaction mixture, "high dilution" (i.e., a large volume of formate ester) is required. However, since the propionaldehyde is rapidly and irreversibly consumed under the reaction conditions, at the conclusion of the reaction, the product (anion 11/12) does not require the presence of a large volume of formate ester. Thus, one might add (at the rate of one drop every few seconds) 10 moles of propionaldehyde (approximately 720 mL) to 10 liters of methyl formate (also containing methyl alcohol and more than 10 moles of sodium methoxide) over a period of 15–20 hours and achieve a high yield of the desired crossed-Claisen condensation product.

In summary, 3-ethoxymethacrolein and related compounds have been prepared in a 2-step, "one-pot" process using low-cost raw materials. The previous route to 3-ethoxymethacrolein, which is an important intermediate in the synthesis of carotenoids., utilized 1-ethoxypropene, a specialty chemical synthesized in two steps from propionaldehyde and triethyl orthoformate, a costly raw material requiring chloroform and 3 equivalents of sodium ethoxide for its manufacture. In contrast, the process of the present invention uses propionaldehyde directly, and utilizes methyl formate in lieu of the costly orthoformate reagent. Since the C-10 dialdehyde intermediate in the manufacture of beta-carotene requires two equivalents of 3-ethoxymethacrolein, the lower cost and fewer steps in the present process can offer a significant advantage in carotenoid manufacture.

DETAILED DESCRIPTION OF THE INVENTION

The following examples are presented for purposes of illustration and should not be construed as limiting the invention which is delineated in the claims.

EXAMPLE I

Preparation of the Sodium Enolate of Methylmalonaldehyde Using Propionaldehyde and Sodium Methoxide in Excess Methyl Formate A solution of sodium methoxide in methyl alcohol was prepared by addition of 134 mg (5.83 mmoles) of metallic sodium (in small pieces, over a period of 10 minutes) to 2.00 mL of methyl alcohol (HPLC-grade, purchased from Aldrich Chemical Co., Milwaukee, Wisc.). This mixture was stirred, while being maintained under a nitrogen atmosphere, until all of the sodium had reacted and hydrogen evolution ceased. After allowing the solution of sodium methoxide in methyl alcohol to cool to room temperature, 15.0 mL (243 mmoles) of methyl formate (spectrophotometric grade, purchased from Aldrich Chemical Co., Milwaukee, Wisc.) was added to the reaction flask, which was equipped with both a septum cap (to allow additions of propionaldehyde to be made using a microliter syringe) and an efficient reflux condenser (to minimize loss of the volatile methyl formate). At that point, the crossed-Claisen condensation was initiated by addition of 1.0 microliter (µL) of freshly-distilled propionaldehyde to the stirred reaction mixture, which was protected from atmospheric moisture throughout the course of the reaction. Every minute, an additional portion of propionaldehyde (1.0 µL) was added until 241 such portions (241×1.0 µL; 3.34 mmoles) of propionaldehyde had been added over a period of 4 hours. The mixture was subsequently stirred at room temperature for 5 minutes to ensure total consumption of propionaldehyde. The sodium enolate of methylmalonaldehyde generated in this manner was not isolated, but was subsequently alkylated as described in the procedure of Example II.

For convenience in microscale reactions, propionaldehyde can also be added in a solution of tetrahydrofuran [THF; 4:1 (v/v) THF:propionaldehyde; 5.0 µL of this solution added every minute]. This modification did not alter the experimental results.

Provided that at least one equivalent of sodium methoxide is present based on the amount of aldehyde utilized in this process, one can continue the micro-additions of propionaldehyde for a considerably longer time, without the need to increase the volume of methyl formate.

Another possible method for slow addition of propionaldehyde to the reaction mixture, that would keep the concentration of propionaldehyde low at all times and enable one to reduce the volume of methyl formate used as the solvent, would be use of a reaction apparatus similar to the one described on page 2864 in an article by M. S. Newman, et al, *J. Org. Chem.*, 40, 2863–2870 (1975). Use of a similar apparatus might enable one to add a solution of propionaldehyde in methyl formate to the base/methyl formate reaction mixture under "high-dilution conditions" without the need for large volumes of solvent.

EXAMPLE II

Preparation of 2-Methyl-3-(2-Methyl-2-Propenoxy)Propenal by Alkylation of the Sodium Enolate of Methylmalonaldehyde To the reaction mixture produced in accordance with Example I was added 5 mL of benzene, a nonpolar solvent (other nonpolar solvents such as heptane, toluene, et al, can also be employed). The reflux condenser connected to the reaction flask was replaced by a micro distillation head; and the mixture was subsequently heated, while being protected from atmospheric moisture, in an oil bath (temperature: 60°–70° C.) to allow removal of the excess methyl formate by distillation (enabling it to be re-cycled for subsequent experiments). Once the formate ester had been removed, 4.0 mL of N,N-dimethylformamide (DMF, spectrophotometric grade, purchased from Aldrich Chemical Company, Milwaukee, Wisc.) was added to the mixture; and the bath temperature was raised to 100° C. to permit distillative removal of methyl alcohol present in the reaction mixture (so that the subsequent alkylation process will proceed more rapidly) along with most of the benzene. After allowing the mixture of the sodium enolate of methylmalonaldehyde in DMF (containing 1–2 mL of benzene) to cool to room temperature, 1.00 mL (10 mmoles) of 3-chloro-2-methylpropene (purchased from Aldrich Chemical Co., Milwaukee, Wisc.) was added. This mixture was then stirred at 50° C. (oil bath temperature), while being maintained under a nitrogen atmosphere, for 15 hours. Although this alkylation will proceed at room temperature, the process was significantly slower and would require prolonged reaction time to obtain a good yield of the desired product.

After cooling the reaction mixture to room temperature, it was diluted with 35 mL of 10% aqueous sodium chloride and the product was isolated by extraction with 30 mL of 1:1 (v/v) hexane:ether. After subsequent washing of the organic layer with 10% aqueous sodium chloride (3×35 mL), it was dried over anhydrous sodium sulfate and filtered. Removal of the volatile organic solvents by evaporation at reduced pressure and subsequent evaporative distillation afforded 338 mg (72 % yield) of the named vinylogous ester: boiling point 65°–80° C. (bath temperature, 0.30 mm). The identity of this novel compound was ascertained by IR and proton NMR analysis. The latter spectrum exhibited a singlet at $\delta 9.22$ (CHO), a quartet (J=1.5 Hz) at $\delta 6.98$ (CH=C), a multiplet at $\delta 5.10$ (CH$_2$=C), a singlet at $\delta 4.55$ (CH$_2$O), a broad singlet at $\delta 1.82$ [$\underline{CH_2}$=C(CH$_3$)], and a doublet (J=1.5 Hz) at $\delta 1.75$ (vinyl methyl bonded to C-2).

To verify that other solvents were suitable for this alkylation process, equivalent volumes of other polar aprotic solvents such as acetonitrile (added to the mixture after distillative removal of methyl formate, methyl alcohol, and most of the benzene), hexamethylphosphoramide and 1-methyl-2-pyrrolidinone were used to replace N,N-dimethylformamide without any significant effect on the yield and purity of the desired product. Dimethyl sulfoxide (DMSO), however, was not a suitable solvent—not surprising since it is well-known that DMSO reacts with alkyl halides, especially at elevated temperature.

The presence of a protic solvent in the alkylation mixture could also be tolerated. Indeed, use of 4:1 (v/v) DMF: methyl alcohol (the latter cosolvent being added after distillative removal of benzene) as the solvent for this alkylation afforded the same product as that obtained using DMF under aprotic conditions. However, use of methyl alcohol as the only solvent for this alkylation process resulted in a slower reaction—although the desired vinylogous ester was ;still obtained.

COMPARATIVE EXAMPLE III

Preparation of the Sodium Enolate of Methylmalonaldehyde Without High Dilution Conditions To a solution of sodium methoxide (5.8 mmoles) in 2.00 mL of methyl alcohol produced from metallic sodium and methyl alcohol in accordance with Example I was added 15.0 mL (243 mmoles) of methyl formate (spectrophotometric grade, purchased from Aldrich Chemical Co., Milwaukee, Wisc.). After equipping the flask with an efficient reflux condenser (to minimize loss of the volatile methyl formate), the crossed-Claisen condensation was initiated by rapid addition of 0.25 mL (3.46 mmoles) of freshly-distilled propionaldehyde. The mixture was subsequently stirred, while being maintained under a nitrogen atmosphere, at room temperature for 2 hours. The sodium enolate of methylmalonaldehyde generated in this manner was not isolated, but was subsequently alkylated using 3-chloro-2-methylpropene (methallyl chloride) in N,N-dimethylformamide as described in the procedure of Example II. After completion of this alkylation (reaction time: 17 hours at 50° C.), the product was isolated as before. Removal of the volatile organic solvents from the hexane-ether extract by evaporation at reduced pressure afforded 206 mg (42.5% yield, based on the expected product) of material, shown by proton NMR analysis to be a complex mixture containing only a minor amount of the desired vinylogous ester (2-methyl-3-(2-methyl-2-propenoxy)propenal]. The major component of the latter mixture was 2-methyl-2-pentenal (the self-aldol condensation product derived from propionaldehyde) accompanied by unidentified polymeric material (perhaps some of which had 'been derived from subsequent transformations of the initial aldol product). The proton NMR spectrum of 2-methyl-2-pentenal exhibited a singlet at $\delta 9.38$ (CHO) and a broad triplet (J=7.5 Hz) at $\delta 6.51$ (CH=C).

In order to ascertain the rate at which propionaldehyde should be added to the sodium methoxide/methyl formate mixture, an identical experiment was conducted except that propionaldehyde (0.25 mL, total amount utilized) was added in 25 "10 µL" portions over a period of 2 hours—i.e., one portion (10 µL) of propionaldehyde was added to the reaction mixture every 5 minutes. Subsequent alkylation using 3-chloro-2-methylpropene in N,N-dimethylformamide as described in the procedure of Example II and isolation of the product in the usual manner afforded 261 mg of crude material, the major component of which was the expected vinylogous ester [2-methyl-3-(2-methyl-2 -propenoxy)propenal]. Subsequent evaporative distillation of this material afforded 207 mg (43% yield) of the named vinylogous ester, the boiling point and spectral properties of which were identical to those exhibited by the product obtained in Example II.

These experiments confirm the fact that, at the time of its addition to the reaction mixture, the concentration of propionaldehyde needs to be kept below 0.01M. Fortunately, the enolate derived from propionaldehyde reacts virtually instantaneously (either with methyl formate or another molecule of propionaldehyde), thereby enabling the addition of propionaldehyde to be conducted at a steady pace. As confirmed by the results of Examples I–II, the time intervals between such additions can be one minute or less. The exact amount of propionaldehyde that can be added in each portion will depend upon the volume of formate ester utilized in the process.

COMPARATIVE EXAMPLE IV

Preparation of the Enolate Derived from Methylmalonaldehyde Using Potassium Methoxide as the Base To a solution of 376 mg (5.4 mmoles) of potassium methoxide (purchased from Aldrich Chemical Co., Milwaukee, Wisc.) in 2.00 mL of methyl alcohol (HPLC-grade) was added 15.0 mL (243 mmoles) of methyl formate (spectrophotometric grade, purchased from Aldrich Chemical Co., Milwaukee, Wisc.). The reaction flask containing this mixture was equipped with both a septum cap (to allow additions of propionaldehyde to be made using a 10-microliter syringe) and an efficient reflux condenser (to minimize loss of the volatile methyl formate). At that point, the crossed-Claisen condensation was initiated by addition of 10 µL of freshly-distilled propionaldehyde to the stirred reaction mixture, which was maintained under a nitrogen atmosphere. Thereafter 10 µL portions of propionaldehyde were added to the reaction mixture every 5 minutes over a period of 2 hours—i.e., 25 portions (10 µL each) of propionaldehyde (3.46 mmoles, total). After the last portion of propionaldehyde was added, the mixture was subsequently stirred at room temperature for an additional 5 minutes. The potassium enolate of methylmalonaldehyde generated in this manner was not isolated, but was subsequently alkylated using 3-chloro-2-methylpropene in N,N-dimethylformamide at 50° C. as described in the procedure of Example II for the analogous sodium enolate of methylmalonaldehyde. The alkylation product was isolated from the reaction mixture in the usual manner, affording 232 mg (48% yield, based on expected product) of material, proton NMR analysis of which indicated that the desired vinylogous ester [2-methyl-3-(2-methyl-2-propenoxy)propenal] comprised less than half of the mixture (i.e., the yield of vinylogous ester was <20%). Furthermore, that spectrum confirmed the presence of a substantial amount of 2-methyl-2-pentenal (the self-aldol condensation product derived from propionaldehyde) [δ9.38 (CHO)] and two additional unidentified products (singlets at δ9.29 and 9.49) not observed in reactions using sodium methoxide as the base. As can be seen from the data in the second part (i.e., second paragraph) of Example III, an identical experiment in which sodium methoxide was used in lieu of potassium methoxide afforded a pure sample of the desired vinylogous ester in >40% yield.

The presence of a substantial amount of self-aldol condensation product derived from propionaldehyde in the crude reaction product of this experiment indicates that problems (involving use of potassium methoxide in lieu of sodium methoxide) arose during the crossed-Claisen condensation (i.e., the first part of the process), not during the subsequent alkylation. Since the initial part of this process is conducted in the presence of a protic solvent ($CH_3OH$) that solvates both $K^+$ and $Na^+$, the two bases should exhibit virtually identical chemical behavior. Although the results are difficult to explain, they were reproduced on several occasions.

EXAMPLE V

Preparation of 2-Methyl-3-Propoxypropenal and Related 3-Alkoxymethacroleins by Alkylation of the Sodium Enolate of Methylmalonaldehyde with 1-Bromopropane and Other Representative Alkyl Halides The sodium enolate of methylmalonaldehyde was prepared using methyl formate, sodium methoxide/methanol solution, and propionaldehyde exactly as described by the procedure of Example I. After addition of 5 mL of benzene to this mixture, excess methyl formate was removed by fractional distillation in accordance with Example II. Once the formate ester had been removed, 4.0 mL of N,N-dimethylformamide (spectrophotometric grade) was added to the mixture and distillative removal of methyl alcohol and most of the benzene was accomplished as outlined in the procedure of Example II. After allowing the mixture of the sodium enolate of methylmalonaldehyde in DMF to cool to room temperature, 1.00 mL (11.0 mmoles) of 1-bromopropane (purchased from Aldrich Chemical Co., Milwaukee, Wisc.) was added. This mixture was then stirred at 62° C. (oil bath temperature), while being maintained under a nitrogen atmosphere, for 18 hours. Isolation of the product as described in the procedure of Example II, followed by evaporative distillation, afforded 350 mg (82% yield) of 2-methyl-3-propoxypropenal: boiling point 60°–68° C. (bath temperature, 0.25 mm). The proton NMR spectrum of this vinylogous ester exhibited a singlet at δ9.15 (CHO), a quartet (J=1.5 Hz) at δ6.94 (vinyl H), a triplet (J=6.5 Hz) at δ4.1 ($CH_2O$), a doublet (J=1.5 Hz) at δ1.72 (vinyl $CH_3$), and a triplet (J=7 Hz) at δ1.02 ($\underline{CH_3}CH_2$).

To verify that other alkylating agents could be used to convert the sodium enolate of methylmalonaldehyde to 3-alkoxymethacroleins, the above procedure was repeated, replacing 1-bromopropane with an equivalent amount of diethyl sulfate (purchased from Aldrich Chemical Co., Milwaukee, Wisc.) or alkyl halides such as 1-chlorobutane and 2-bromobutane. All such reactions proved to be successful, although the rate at which alkylation occurred varied with the structure of the reactant. Alkylation of the sodium enolate of methylmalonaldehyde using diethyl sulfate proceeded to completion in less than 15 hours at temperatures between 30°–40° C. Use of the less reactive 1° alkyl chloride (1-chlorobutane) afforded the desired 3-butoxymethacrolein, but required a reaction time of more than 30 hours at 65° C. In order to reduce the time required for this alkylation using a 1° alkyl chloride, either the reaction temperature should be increased or else one might add a catalytic amount of an alkali-metal bromide (NaBr or KBr) or iodide (NaI) salt to the reaction mixture. Alkylation of the sodium enolate of methylmalonaldehyde in DMF was also successfully achieved by use of a representative 2° alkyl halide (2-bromobutane) at a reaction temperature of 70° C.

EXAMPLE VI

Preparation of the Sodium Enolate of Methylmalonaldehyde Using Propionaldehyde and Sodium Ethoxide in Excess Ethyl Formate A solution of sodium ethoxide in ethyl alcohol was prepared by addition of 150 mg (6.52 mmoles) of metallic sodium (in small pieces, over a period of 5–10 minutes) to 3.00 mL of absolute ethyl alcohol. This mixture was stirred, while being maintained under a nitrogen atmosphere, until all of the sodium had reacted and hydrogen evolution ceased. After allowing the solution to cool to room temperature, 20 mL (approximately 250 mmoles) of ethyl formate (97% purity, purchased from Aldrich Chemical Co., Milwaukee, Wisc.) was added to the reaction flask, which was equipped with both a septum cap (to allow additions of propionaldehyde to be made using a 10 µL syringe) and an efficient reflux condenser. After placing the reaction flask in an oil bath (temperature: 45° C.), the crossed-Claisen condensation was initiated by addition of 10 µL of freshly-distilled propionaldehyde to the stirred reaction mixture. Every 5 minutes, an additional portion (10 µL) of propionaldehyde was added until 25 such portions (25×10 µL; 3.46 mmoles) of propionaldehyde had been added over a period of 2 hours. The mixture was subsequently stirred at 45° C. for 5 minutes to ensure total consumption of propionaldehyde. The sodium enolate of methylmalonaldehyde generated in this manner was not isolated, but was subsequently alkylated using 3-chloro-2-methylpropene as described below.

After cooling the above reaction mixture to room temperature, 8.0 mL of benzene was added to the flask; and the reflux condenser was replaced by a micro distillation head. This mixture was subsequently heated in an oil bath (temperature: 70° C.) to allow removal of the excess ethyl formate by distillation (allowing it to be re-cycled for subsequent experiments). Once the formate ester had been removed, 4.0 mL of N,N-dimethylformamide (DMF, spectrophotometric grade) was added to the mixture and the bath temperature was raised to 100° C. to permit distillative removal of ethyl alcohol along with most of the benzene. After allowing the mixture of the sodium enolate of methylmalonaldehyde in DMF (containing 1–2 mL of benzene) to cool to room temperature, 1.00 mL (10.1 mmoles) of 3-chloro-2-methylpropene was added. This mixture was then stirred at 50° C. (oil bath temperature), while being maintained under a nitrogen atmosphere, for 18 hours. After cooling the mixture to room temperature, it was diluted with 35 mL of 10% aqueous sodium chloride and the product was isolated by extraction with 1:1 (v/v) hexane:ether using the procedure described in Example II. Subsequent evaporative distillation of the crude product (260 mg) afforded 201 mg (41% yield) of 2-methyl-3-(2-methyl-2-propenoxy)propenal, the boiling point and spectral properties of which were identical to those exhibited by the product obtained in Example II.

EXAMPLE VII

Conversion of the Sodium Enolate of Methylmalonaldehyde to a Vinylogous Ester by Acidification and Subsequent Treatment with an Alcohol The crossed-Claisen condensation was effected by addition of 10 µL portions of propionaldehyde, one portion every 5 minutes, over a period of 2 hours to a mixture containing 6.0 mmoles of sodium methoxide (prepared in situ using metallic sodium as described in the procedure of Example I) in 2.0 mL of methyl alcohol and 15.0 mL of methyl formate (spectrophotometric grade). After addition of the last portion of propionaldehyde, the mixture was subsequently stirred at room temperature for 5 minutes to ensure total consumption of propionaldehyde. The sodium enolate of methylmalonaldehyde generated in this manner was not isolated, but instead was converted to a vinylogous ester using the procedure described below.

After adding 8.0 mL of benzene to the reaction mixture, the reflux condenser connected to the reaction flask was replaced by a micro distillation head. The mixture was subsequently heated, while being protected from atmospheric moisture, to distill out the excess methyl formate, methyl alcohol present in the mixture, and most of the benzene. Once the volume of solvent in the flask had decreased to approximately 3 mL, the mixture was cooled to room temperature; and 1.00 mL ( 10.8 mmoles) of isobutyl alcohol, followed by 6.0 mL of benzene (spectrophotometric grade), was added to the flask. This mixture was then acidified by addition (in portions) of 1.33 g (7.0 mmoles) of p-toluenesulfonic acid monohydrate to liberate methylmalonaldehyde. (Gaseous HCl may be preferred for this neutralization during a large-scale process). This solution of methylmalonaldehyde containing isobutyl alcohol and a catalytic amount of p-toluenesulfonic acid was subsequently transferred to a one-neck round-bottom flask equipped with a Dean-Stark trap (filled with benzene). The acidified reaction mixture was then heated at reflux for 2.5 hours with continuous azeotropic removal of water. The cooled mixture was subsequently diluted with 30 mL of 1:1 (v/v) hexane:ether and washed in successive order with 1:1 (v/v) 1M aqueous sodium hydroxide: 10% aqueous sodium chloride (1×20 µL), 10% aqueous sodium chloride (20 mL), and saturated brine (20 mL). The washed organic layer was then dried over anhydrous sodium substrate and filtered. Removal of the volatile organic solvents under reduced pressure afforded 190 mg (39% yield, uncorrected for impurities) of crude material shown by proton NMR analysis to be comprised of the desired vinylogous ester [3-isobutoxymethacrolein] and unidentified by-products (approximately one-half of the mixture). The vinylogous ester was characterized by an NMR spectrum that exhibited a singlet at δ9.21 (CHO), a quartet (J=1.5 Hz) at 6.96 (vinyl H), and a doublet (J=6.5Hz) at δ3.92 (OCH$_2$).

No further effort was made to develop this process to increase the yield, although if one wishes to avoid use of alkyl halides in the preparation of 3-alkoxymethacroleins, this route would be attractive. Obviously, the yield would have been increased significantly by addition of smaller portions of propionaldehyde (as in Example I) to the base/formate ester mixture—thereby enhancing the yield in the crossed-Claisen condensation.

I claim:

1. A process for forming sodium methylmalonaldehyde comprising:

A) forming a first reaction mixture comprising:
   i) one equivalent of a sodium alkoxide having the formula NaOR';
   ii) an alkyl formate of the formula HCOOR, wherein the molar quantity of said formate is in excess of the molar quantity of said alkoxide; and
   iii) an alcohol cosolvent of the formula R'OH;

wherein R and R', which can be the same or different, are $C_1$–$C_4$ alkyl;

B) slowly adding propionaldehyde to said first reaction mixture at a rate whereby the molar ratio of alkyl formate to propionaldehyde is greater than 5000:1, while maintaining said reaction mixture at a temperature of between about 15° C. and about 50° C.

2. The process of claim 1 wherein said alkoxide is sodium methoxide, said cosolvent is methyl alcohol, and said alkyl formate is methyl formate.

3. The process of claim 2 wherein the sodium methoxide is formed, in situ, by the addition of metallic sodium to methyl alcohol.

4. The process of claim 1 wherein propionaldehyde is dispersed in a solvent comprising tetrahydrofuran.

5. A process for forming 3-alkoxy-2-methylpropenals comprising:
  A) forming a first reaction mixture comprising:
    i) one equivalent of a sodium alkoxide having the formula NaOR';
    ii) an alkyl formate of the formula HCOOR, wherein the molar quantity of said formate is in excess of the molar quantity of said alkoxide; and
    iii) an alcohol cosolvent of the formula R'OH;
  wherein R and R', which can be the same or different, are $C_1$–$C_4$ alkyl;
  B) slowly adding propionaldehyde to said first reaction mixture at a rate whereby the molar ratio of alkyl formate to propionaldehyde is greater than 5000:1, while maintaining said reaction mixture at a temperature of between about 15° C. and about 50° C., thereby forming sodium methylmalonaldehyde;
  C) forming a second reaction mixture in an organic solvent comprising:
    i) the sodium methylmalonaldehyde of step (B); and
    ii) a reactant selected from the group consisting of one or more of the following:
      a) a halide of the formula R''—X, wherein X is chloride or bromide, and R'' is $C_1$–$C_{10}$ alkyl, $C_3$–$C_{10}$ allylic or benzyl; and
      b) a sulfate ester of the formula:

wherein R''' is $C_1$–$C_4$ alkyl; and
  D) maintaining said second reaction mixture at a temperature in the range of about 15° C. to about 100° C.

6. The process of claim 5 wherein said organic solvent in step C comprises a polar, aprotic solvent.

7. The process of claim 6 wherein said organic solvent further includes a nonpolar solvent.

8. The process of claim 7 wherein said nonpolar solvent is selected from benzene, toluene and xylene.

9. The process of claim 6 wherein said polar, aprotic solvent is selected from the group consisting of: N,N-dimethylformamide, acetonitrile, 1,4-dioxane and 1-methyl-2-pyrrolidinone.

10. The process of claim 5 wherein said organic solvent comprises elements ii and iii of step A.

11. The process of claim 5 wherein said alkoxide is sodium methoxide, said cosolvent is methyl alcohol, and said alkyl formate is methyl formate.

12. The process of claim 11, further including the steps:
  adding a nonpolar solvent to the first reaction mixture at the completion of step B;
  distilling the nonpolar-solvent-containing mixture by heating it to a temperature in excess of 35° C. to remove methyl formate;
  adding a polar aprotic solvent to said nonpolar-solvent-containing mixture at the completion of said distillation step; and
  heating said polar aprotic-solvent-containing mixture to a temperature exceeding 65° C. to remove excess methyl alcohol.

13. The process of claim 12 wherein said nonpolar solvent is selected from the group consisting of: benzene, heptane, toluene and mixtures thereof.

14. The process of claim 12 wherein said polar, aprotic solvent is selected from the group consisting of: N,N-dimethylformamide, acetonitrile, 1,4-dioxane, 1-methyl-2-pyrrolidinone, and mixtures thereof.

15. The process of claim 5 wherein R'' is selected from the group: methyl, ethyl, propyl, isopropyl, butyl, isobutyl, sec-butyl, allyl, methallyl and mixtures thereof.

16. The process of claim 5 wherein said sulfate ester is methyl sulfate.

17. A process for forming 3-alkoxy-2-methylpropenals comprising:
  A) forming a first reaction mixture comprising:
    i) one equivalent of a sodium alkoxide having the formula NaOR';
    ii) an alkyl formate of the formula HCOOR, wherein the molar quantity of said formate is in excess of the molar quantity of said alkoxide; and
    iii) an alcohol cosolvent of the formula R'OH;
  wherein R and R', which can be the same or different, are $C_1$–$C_4$ alkyl;
  B) slowly adding propionaldehyde to said first reaction mixture at a rate whereby the molar ratio of alkyl formate to propionaldehyde is greater than 5000:1, while maintaining said reaction mixture at a temperature of between about 15° C. and about 50° C., thereby forming sodium methylmalonaldehyde;
  C) forming a second reaction mixture in an organic solvent comprising:
    i) the sodium methylmalonaldehyde of step (B); and
    ii) $C_1$–$C_4$ primary or secondary alcohol and at least one equivalent of an acid having a $pK_a$ of less than 5; and
  D) heating said reaction mixture with continuous removal of water.

18. The process of claim 17 wherein said acid having a $pK_a$ of less than 5 is selected from the group consisting of p-toluenesulfonic acid, HCl or mixtures thereof.

19. The process of claim 17 wherein said alcohol of step C(ii) comprises isobutyl alcohol or butyl alcohol.

20. The process of claim 17 wherein said organic solvent further includes a nonpolar solvent.

21. The process of claim 20 wherein said nonpolar solvent is selected from benzene, toluene and xylene.

* * * * *